United States Patent [19]
Engel

[11] Patent Number: 5,993,375
[45] Date of Patent: Nov. 30, 1999

[54] MODULAR MAGNETIC THERAPY DEVICE

[76] Inventor: Peter H. Engel, 144 N. Roberson Blvd., Los Angeles, Calif. 90048-3102

[21] Appl. No.: 09/030,184

[22] Filed: Feb. 25, 1998

[51] Int. Cl.$^6$ .............................. A61N 1/00; A61B 17/52
[52] U.S. Cl. .................................................. 600/15; 600/9
[58] Field of Search ........................ 600/15, 9; 128/876, 128/873, 872, 869; 602/41, 78

[56] References Cited

U.S. PATENT DOCUMENTS

| | | | |
|---|---|---|---|
| 4,549,532 | 10/1985 | Baermann | 600/15 |
| 5,450,858 | 9/1995 | Zablotsky et al. | 600/15 |
| 5,746,213 | 5/1998 | Marks | 600/499 |

OTHER PUBLICATIONS

NDL BIOflex advertisement, two pages.
Magnetherapy, Inc. Tectonic Magnets advertisement, two pages.

Primary Examiner—Cary O'Connor
Assistant Examiner—Navin Natnithithadha
Attorney, Agent, or Firm—Fattibene & Fattibene; Paul A. Fattibene; Arthur T. Fattibene

[57] ABSTRACT

A pad having a permanent magnet therein and a first fastener material on one side and a mating fastener material on the other side. A plurality of pads are fastened together along their perimeters forming any desired shape. The plurality of pads are placed adjacent to a portion of the body creating a desired magnetic field for use in magnetic therapy. An elastic wrap or bandage is used to hold the plurality of attached pads in position adjacent to the body. The pad has a foam material on one side and a mesh material on the other. A VELCRO fastener material is preferably used for attaching the plurality of pads together. The modular pad makes easy placement of permanent magnets used in magnetic therapy without the need for a variety of special purpose pads shaped to fit the desired portion of the body. Magnetic therapy can therefore be practiced with greater flexibility and reduced cost.

13 Claims, 3 Drawing Sheets

MODULAR MAGNETIC THERAPY DEVICE

FIELD OF THE INVENTION

The present invention relates in general to a permanent magnet device used in magnetic therapy, and more particularly to a modular permanent magnet pad used to promote healing and reduce pain.

BACKGROUND OF THE INVENTION

The use of magnetic fields to promote healing and reduce pain is well known in the medical profession. There have been many studies in which it has been found that the use of a magnetic field can speed up post-operative healing. Additionally, there have been many studies in which the use of a magnetic field helps to alleviate pain. While there have been many different theories advanced as to why magnetic therapy works, it is still not clearly understood exactly how magnetic therapy aids in healing and in reducing pain. However, it is clear that many people's lives have been greatly improved by the use of magnetic therapy. Many devices have, therefore, been developed to practice magnetic therapy. One such magnet device for therapeutic use is disclosed in U.S. Pat. No. 4,549,532 entitled "Flexible Magnetic Sheet for Therapeutic Use" issuing to Baermann on Oct. 29, 1985, which is herein incorporated by reference. Therein disclosed is a permanent magnet sheet having alternating poles for applying a magnetic field to portions of the body for therapeutic purposes. Magnetic therapy devices generally take the form of placing a specially adapted permanent magnet pad adjacent a particular portion of the body. Accordingly, there are separate specialized products specifically adapted for back pain, neck pain, elbow pain, wrist pain, knee pain, and other various parts of the body. Often, an individual wishing to benefit from magnetic therapy is required to purchase a relatively large number of specialized devices for placing a permanent magnet adjacent different portions of the body. This is often inconvenient and expensive. Accordingly, there is a need for an improved permanent magnet device for use in magnetic therapy that can be applied easily to different locations of the body.

SUMMARY OF THE INVENTION

The present invention is directed to a modular pad having a plurality of permanent magnets placed within the pad. The pad has one planar surface with a perimeter of a fastening material and an opposing planar surface of a mating fastening material. The fastening material may be a hook-type fastener and the mating fastening material may be a loop-type fastening material. One such fastening material is commonly known as a VELCRO fastener. This pad structure permits a plurality of pads to be fastened together in any desired configuration by attaching the fastener material on one surface to the mating fastener material on the other surface. A wrap may be used to hold the attached pads adjacent any desired portion of the body requiring treatment.

Accordingly, it is an object of the present invention to eliminate the need for a variety of special purpose magnetic therapy devices.

It is another object of the present invention to make magnetic therapy more cost effective and convenient.

It is an advantage of the present invention that the modular pads may be configured in any shape.

It is another advantage of the present invention that the magnetic field pattern and intensity can be varied.

It is a feature of the present invention that a perimeter of one surface has a fastener material and an opposing surface has a mating fastener material.

It is another feature of the present invention that one surface is padded and the opposing surface has a mesh covering.

These and other objects, advantages, and features will become readily apparent in view of the following detailed description.

DETAILED DESCRIPTION OF THE PREFERRED EMBODIMENTS

Figure 1:
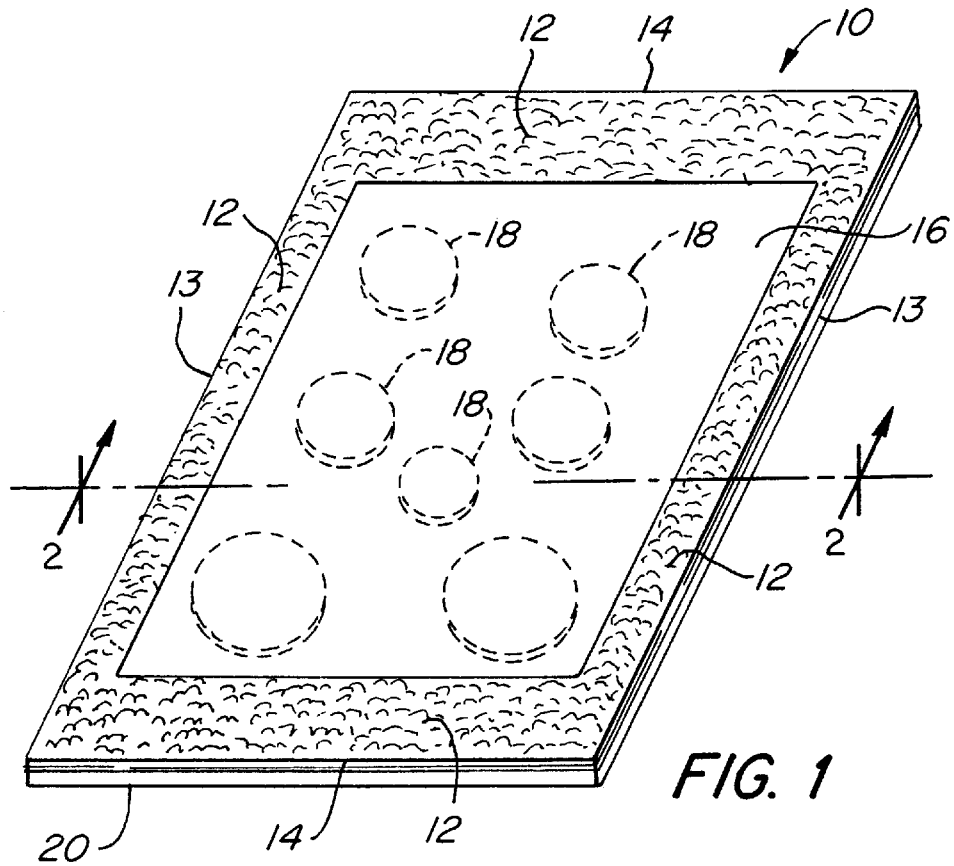
FIG. 1 is a perspective view of a single pad of the present invention.
Figure 1A:
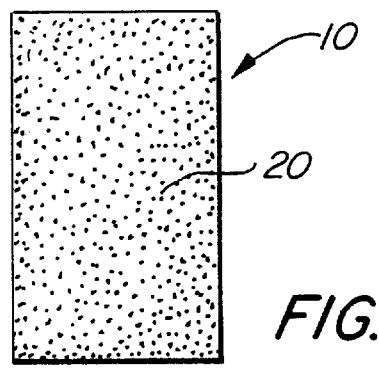
FIG. 1a is a plan view of a single pad of the present invention.

FIG. 1 illustrates a pad 10 having a first and second substantially planar surface. A first planar surface has longitudinal edges 13 with a fastener material 12 thereon, such as a hook-type fastener material. The first planar surface also has lateral edges 14 with a fastener material 12 thereon, which may also be a hook-type fastener material. Accordingly, the first planar surface of pad 10 has a perimeter of a first fastener material, such as a hook-type fastener material. Bounded by the longitudinal edges 13 and the lateral edges 14 is a bounded portion 16. The bounded portion 16 is covered with a mesh fabric. Placed within this bounded portion 16 and covered by the mesh fabric are a plurality of permanent magnets 18. The permanent magnets 18 may take a variety of shapes such as square or rectangular, but are illustrated as being circular. The permanent magnets may be made of any conventional permanent magnet material such as Ceramic 5, having a Gauss rating of 3950. However, magnets 18 may also be made of a variety of known rare earth materials used to make a permanent magnet and having a relatively strong magnetic field. On the opposing planar surface of pad 10 is a mating fastener material 20, such as a pile or loop-type fastener material. The hook-type and mating loop-type fastener materials are generally known and sold under the trademark VELCRO fastener. While hook-type and mating loop-type fastener materials are preferred, any other fastener and mating fastener materials may be used. FIG. 1a is a plan view of a single modular pad 10 illustrating the opposing substantially planar surface having the entire surface covered with the pile or loop-type mating fastener material 20.

Figure 2:
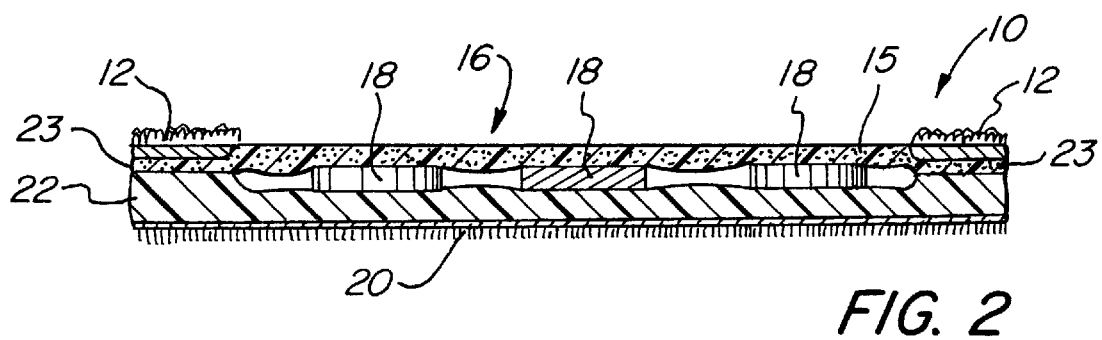
FIG. 2 is a cross section taken along line 2–2 in FIG. 1.

FIG. 2 is a cross section taken along line 2—2 in FIG. 1 and better illustrates the construction of the pad 10. A foam pad 22, such as neoprene, has a pile or loop material 20 attached thereto. The foam pad 22 forms a substantially planar surface. The mating fastener pile or loop material 20 preferably covers the entire planer surface of the one side of the foam pad 22. This permits a mating hook-type fastener material 12 to be attached anywhere on the surface. Additionally, the foam pad 22 is sufficiently flexible to adapt to different portions of the body. Attached to the opposing side or planer surface of foam pad 22 is a mesh fabric 15 forming a bounded portion 16. Attached to the mesh fabric 15 along both the longitudinal edges and lateral edges is fastener material 12. The fastener material 12 may be adhered to the mesh fabric 15 by any conventional means, such as stitching 23. Accordingly, a pocket or space is formed between the mesh fabric 15 and the foam material 22 within which is placed a plurality of permanent magnets 18. The foam pad 22 is attached to the mesh fabric 16 by adhesive or any other conventional means, such as stitching 23.

Figure 3:
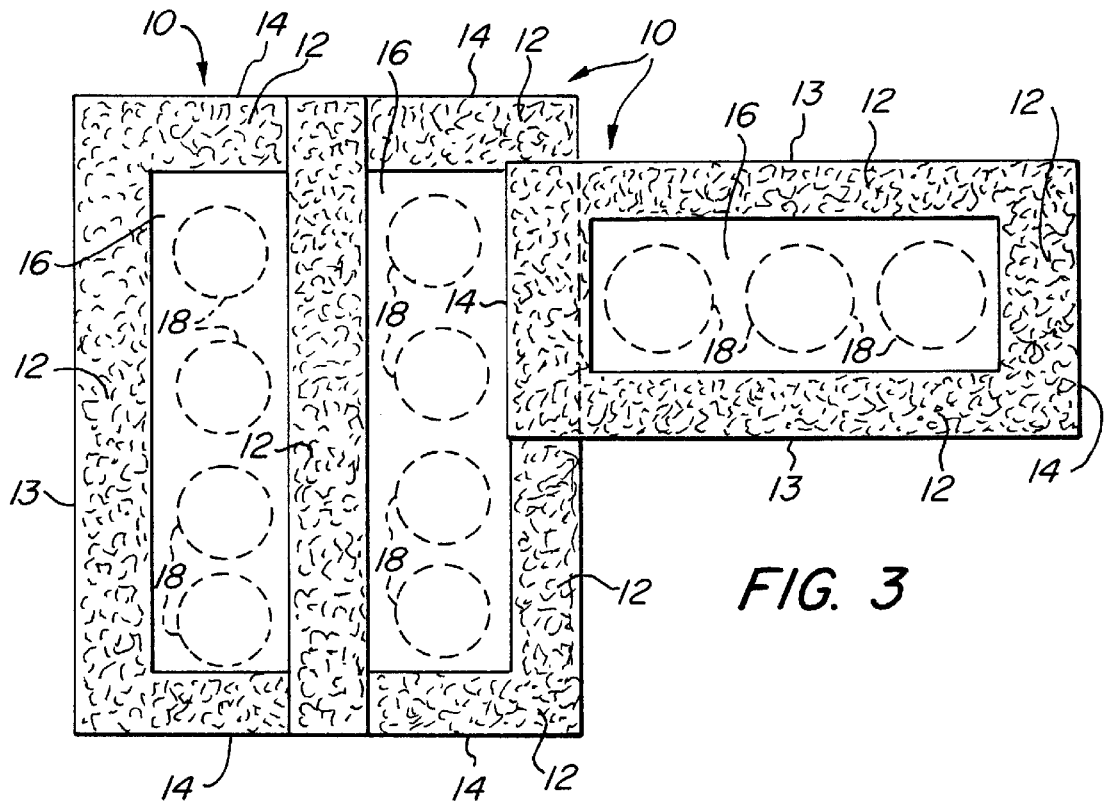
FIG. 3 is a plan view illustrating a plurality of pads attached together.

FIG. 3 is a plan view illustrating a plurality of pads 10 attached or fastened together. Two pads 10 are attached by longitudinal edges 13 and another pad 10 is attached by a lateral edge 14 to the longitudinal edge 13 of another pad. A fastener material 12 along the perimeter edges of the pads 10 is used to attach to the opposing surface of another pad having a mating pile or loop-type fastener material 20, as illustrated in FIG. 1 and FIG. 2. Preferably, the one fastener material is a hook type fastener material and the other mating fastener material is a loop-type fastener material. Such a hook-type and loop-type fastener material are commonly referred to as, and available under the trademark VELCRO fasteners. Clearly, the fastener materials could be reversed such that the loop or pile fastener material is placed around the peripheral edge of the pads 10 and the mating hook-type fastener material is placed on the opposing planar surface of the pads 10. Accordingly, the structure of the pads 10 of the present invention permit the pads 10 to be fastened together in a modular manner forming any desired shape. This permits the creation of a magnetic therapy device having any desired shape or magnetic field for placement adjacent any part of the body. Additionally, the pads 10 may be stacked one on top of another to vary the magnetic field intensity applied to a part of the body.

Figure 4:
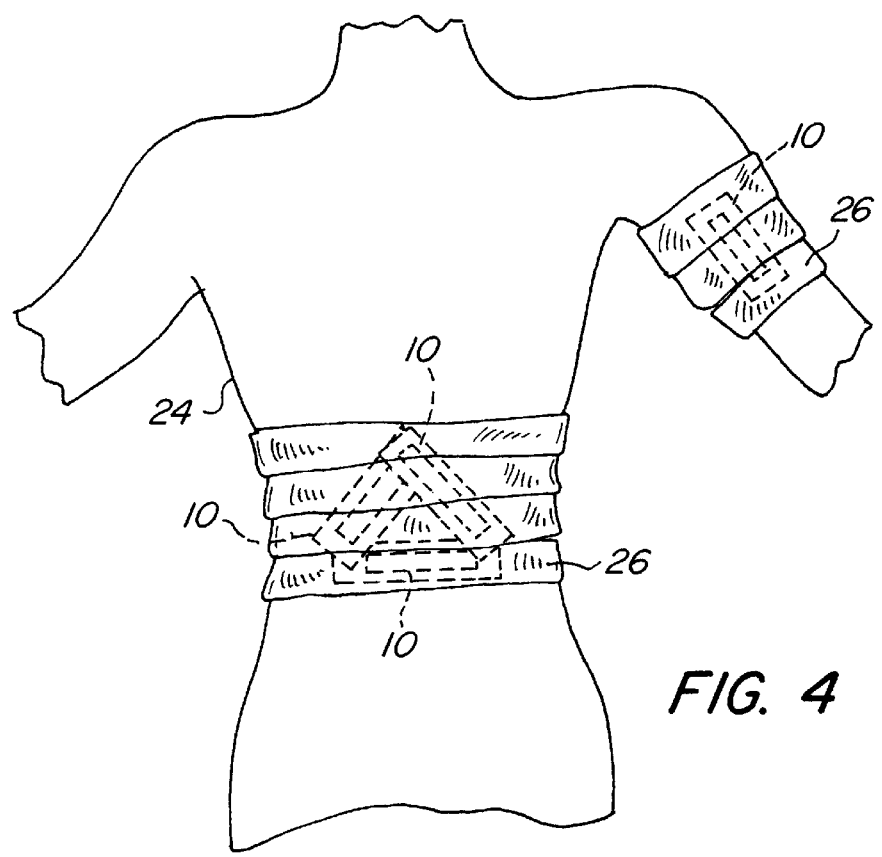
FIG. 4 is a schematic illustration of the application of the present invention to a body.

FIG. 4 schematically illustrates the placement of a plurality of modular pads 10 on the body of a person. Three pads 10 are illustrated configured in a triangular shape and placed on the torso of a body 24. A wrap 26 is used, such as an elastic bandage or other suitable or equivalent material, to hold the pads 10 in position adjacent the area of the body to be treated. Additionally illustrated, is the placement of a single pad 10 on a portion of an arm of the body 24. This pad 10 is similarly held in position with an elastic bandage or a wrap 26. Accordingly, it should be appreciated that a plurality of pads 10 containing permanent magnets can be configured in any desired shape and positioned adjacent any portion of the body 24. Magnetic therapy can therefore be provided to any portion of the body without the need for many different specialized devices. Additionally, the modular pads 10 may be positioned in any desirable configuration to provide a predetermined magnetic field location and intensity, depending upon the therapy desired or needs of the individual.

Figure 5:
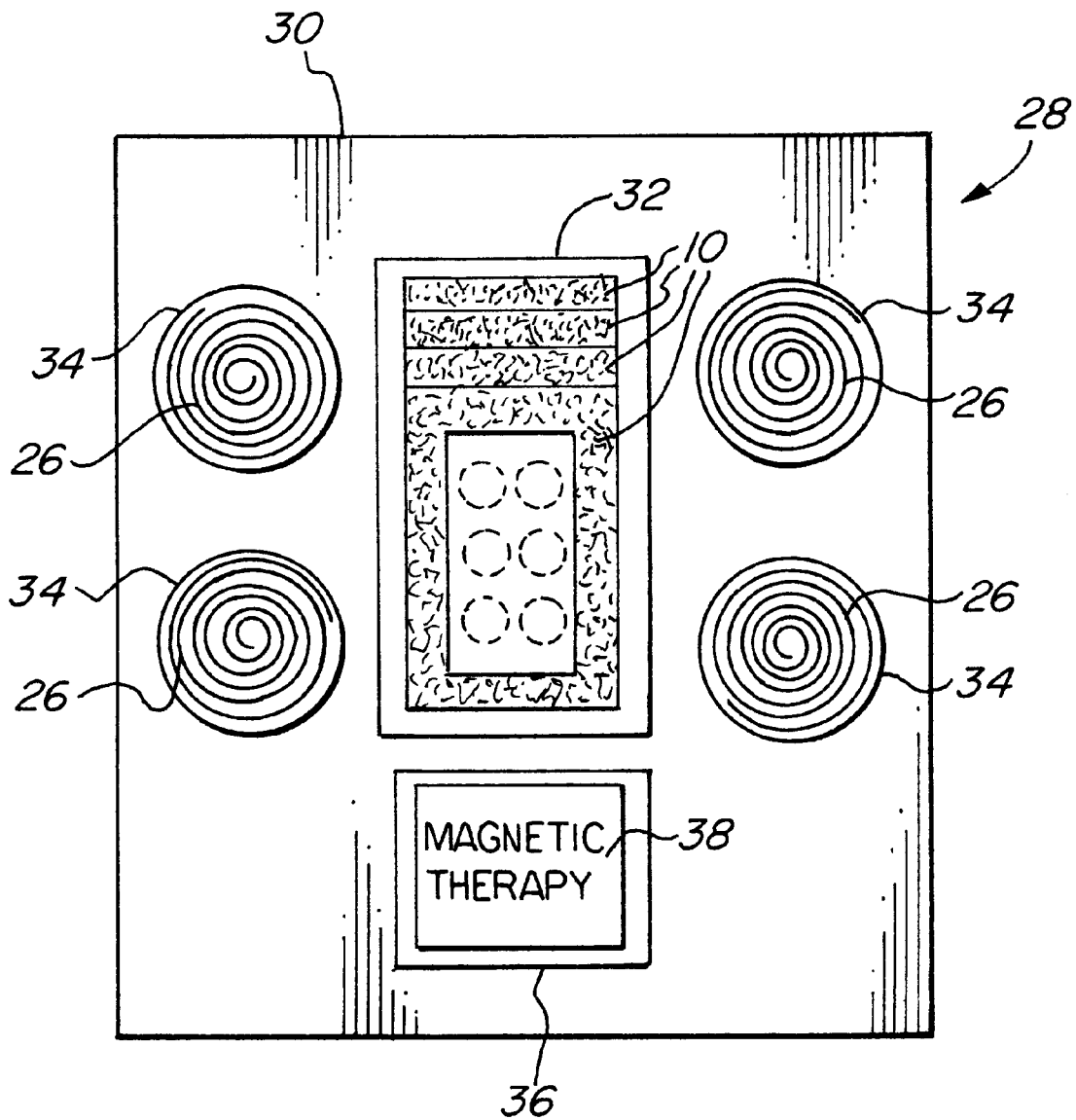
FIG. 5 is a plan view of a magnetic therapy kit.

FIG. 5 is a plan view of a magnetic therapy kit 28. A plastic tray 30 has a pad well 32 therein for holding a plurality of pads 10. A plurality of wrap wells 34 are formed in the plastic tray 30, each for holding a coiled elastic wrap 26. A book well 36 may also be formed in the plastic trays 30 for holding a magnetic therapy book 38. The kit 28 provides a convenient package providing the required items for applying magnetic therapy to any part of the body.

The present invention greatly facilitates the practice of magnetic therapy. The present invention provides great flexibility in the application to different parts of the body a magnetic field to reduce or alleviate pain or to promote healing. The structure of the present invention permits the modular pads to be very easily attached together, forming any desired shape and magnetic field. This provides great flexibility in applying a magnetic field, as well as making magnetic therapy more economical, because many different specialized pads for different parts of the body do not have to be individually purchased. Additionally, the present invention provides for the placement of a permanent magnet adjacent portions of the body for which there are currently no available specialized pads.

While the present invention has been described with respect to several preferred embodiments, it should be appreciated that various modifications may be made without departing from the spirit and scope of the present invention.

What is claimed is:

1. A magnetic therapy device comprising:
    a pad having a first surface and a second surface, said pad having a perimeter;
    a permanent magnet positioned within said pad;
    a first part of a fastener material extending along an edge around the entire perimeter of said pad on the first surface; and
    a second part of a fastener material extending along an edge around the entire perimeter of said pad on the second planar surface;
    whereby a plurality of said pads can be fastened together to form a desired shape and placed against a portion of a body for magnetic therapy.

2. A magnetic therapy device as in claim 1 wherein:
    said pad has a quadrilateral shape.

3. A magnetic therapy device as in claim 2 wherein:
    said quadrilateral shape is a rectangle.

4. A magnetic therapy device as in claim 1 wherein:
    said first part of a fastener material is a hook fastener material.

5. A magnetic therapy device as in claim 1 wherein:
    said second part of a fastener material is a loop fastener material.

6. A magnetic therapy device as in claim 1 wherein:
    the second part of a fastener material covers the entire second surface.

7. A pad used in magnetic therapy comprising:
    a planar foam substrate;
    a loop fastener material placed over the entire surface of one side of said planar foam substrate;
    a mesh material attached to said planar foam substrate forming a pocket;
    a plurality of permanent magnets placed within the pocket formed between said planar foam substrate and said mesh material; and
    a hook fastener material placed around the perimeter of said mesh material,
    whereby a plurality of pads can be fastened together by attaching said loop fastener material on one pad to said mating hook fastener material of another pad and placed against the body for magnetic therapy.

8. A pad used in magnetic therapy as in claim 7 further comprising:
    means for attaching said pad to a human body.

9. A method of applying a magnetic field to a human body comprising the steps of:
    attaching a plurality of pads containing permanent magnets together in a predetermined configuration;
    placing the attached plurality of pads adjacent a desired portion of the human body; and
    holding the attached plurality of pads in place,
    whereby magnetic therapy can be applied to any part of the human body to help promote healing and reduce pain.

10. A magnetic therapy kit comprising:

a tray;

a plurality of pads placed within said tray, each of said plurality of pads having a permanent magnet placed therein, a first fastener material placed around the perimeter on one surface of each of said plurality of pads, and a second mating fastener material placed on the other opposing surface of each of said plurality of pads; and a wrap placed within said tray, whereby said plurality of pads can be fastened together and placed adjacent any portion of the body.

11. A magnetic therapy kit as in claim 10 further comprising:

a book about magnetic therapy.

12. A magnetic therapy device comprising:

a plurality of pads, each of said plurality of pads having a first surface and a second surface, each of said plurality of pads having a perimeter;

a permanent magnet positioned within each of said plurality of pads;

a first part of a fastener material extending around the perimeter of each of said plurality of pads on the first surface;

a second part of a fastener material extending around the perimeter of each of said pad on the second planar surface;

whereby said plurality of pads can be fastened together to form a desired shape and placed against a portion of a body for magnetic therapy.

13. A magnetic therapy device as in claim 12 further comprising:

a wrap, whereby said wrap holds said plurality of pads against the portion of the body.

* * * * *